(12) United States Patent
Seder et al.

(10) Patent No.: US 6,484,345 B2
(45) Date of Patent: Nov. 26, 2002

(54) VOICE PROSTHESIS BRUSH

(75) Inventors: Edmund V. Seder, Santa Barbara, CA (US); Christopher S. Mudd, Santa Barbara, CA (US)

(73) Assignee: Helix Medical, Inc., Carpinteria, CA (US)

( * ) Notice: Subject to any disclaimer, the term of this patent is extended or adjusted under 35 U.S.C. 154(b) by 0 days.

(21) Appl. No.: 09/783,664

(22) Filed: Feb. 13, 2001

(65) Prior Publication Data

US 2002/0108195 A1 Aug. 15, 2002

(51) Int. Cl.[7] ............................................... B08B 9/043
(52) U.S. Cl. ..................................... 15/104.2; 15/206
(58) Field of Search ....................... 15/104.05, 104.066, 15/104.16, 104.2, 206

(56) References Cited

U.S. PATENT DOCUMENTS

| 2,232,358 A | * | 2/1941 | Baerer |
| 2,496,381 A | * | 2/1950 | Cummings |
| 3,613,664 A | * | 10/1971 | Willson |
| 4,819,291 A | * | 4/1989 | Gunjan |
| 4,889,106 A | * | 12/1989 | Watanabe |
| 5,003,657 A | * | 4/1991 | Boiteau et al. |
| 5,253,386 A | * | 10/1993 | Lalonde |
| 5,578,083 A | | 11/1996 | Laguette et al. |

* cited by examiner

Primary Examiner—Terrence R. Till
(74) Attorney, Agent, or Firm—Marvin E. Jacobs

(57) ABSTRACT

A brush for a voice prosthesis containing a reduced diameter hard cartridge disposed in the distal section of a soft outer body. The brush includes a reduced diameter distal brush section mounted in a rod having a distal end face larger than the diameter of the cartridge such that the extension of the end of the brush into the opposed esophageal wall is prevented.

5 Claims, 1 Drawing Sheet

VOICE PROSTHESIS BRUSH

TECHNICAL FIELD

This invention relates to a voice prosthesis accessory device and, more particularly this invention relates to an improved brush for cleaning long-dwelling voice prosthesis while installed in a patient.

BACKGROUND OF THE INVENTION

There are several options for restoring speech to patients who have had their larynx removed. One procedure is to surgically create a puncture of fistula between the trachea and the esophagus. A trachea voice prosthesis containing a one-way valve such as a BLOM-SINGER® voice prosthesis is inserted into the tracheoesophageal fistula. The one-way valve protects the airway during swallowing but opens under positive pressure. The voice prosthesis, thus, permits a patient to divert air from the lungs into the esophagus and out through the mouth. Speech is created during passage of air through the upper part of the esophagus.

The prosthesis maintains the fistula open, transfers air from the trachea to the esophagus for voice production and prevents esophageal leakage into the trachea during swallowing. The oral cavity which extends into the throat has a high microbial population. However, the prosthesis being in contact with moisture in a hot, dark, nutrient rich environment is subject to growth of commonly found microorganisms, typically Candida, on the valve and the retaining flange. The microbial attack is currently being studied. The microbial attack organisms and sequence of events are quite complex and are still undetermined. The microbial growth on and into the soft silicone resin can interfere with function of the valve and cause it to leak. The fouled device must be cleaned or discarded and replaced with a new device.

The current low pressure voice prosthesis can be removed by the patient every few days and can be replaced with a clean prosthesis. The removed prosthesis is soaked in hydrogen peroxide to sterilize the valve and flange. Some patients however, have difficulty managing frequent removal and reinsertion of the prosthesis. Others, who are physically handicapped are not able to remove, sterilize, or reinsert the prosthesis.

A longer dwelling, low pressure voice prosthesis has been developed that can remain in place in the tracheoesophageal fistula for many weeks or months, depending on the patient and conditions of use. The patient can confidently use the prosthesis for longer periods. The longer dwelling voice prosthesis is not removable by the patient. Trips to a health care specialist to remove and replace the prosthesis are greatly extended providing increased comfort and lower cost to the patient.

STATEMENT OF THE PRIOR ART

Between trips to a health care specialist, the voice prosthesis can be cleaned by scrubbing the central passage and valve of the prosthesis with a brush. However, the currently available brush system can pass through the valve and can injure the opposed esophageal wall even though this proximal end of the wire brush is coated with resin and a washer is disposed at the start of the bristles.

STATEMENT OF THE INVENTION

An improved brush for a voice prosthesis is provided by this invention. The brush is so structured that the bristled end of the brush is prevented from reaching the esophageal wall. The brush is adapted to be used with a voice prosthesis containing a cylindrical rigid cartridge within a soft outer body as disclosed in commonly assigned U.S. Pat. No. 5,578,083, the disclosure of which is expressly incorporated herein by reference. The brush can also be used with voice prosthesis containing a rigid valve seat within a soft outer body. The proximal end of the cartridge or valve seat extends into the central passage of the prosthesis forming a stop surface. A reduced diameter passage extends distally from the stop surface. The proximal end of the brush includes a rod from which the bristles extend. The proximal end of the rod is larger than the passage and abuts on the stop surface. The bristles, which can be mounted on a coiled wire, extends through the cartridge preferably up to the distal flange of the body of the prosthesis such that the bristles contact the valve element. The bristled section can be longer than the cartridge or valve seat and rear portion of the body. Preferably the bristle portion ends at about the rear flange of the prosthesis or at the end of a distal hood, if present.

These and many other features and attendant advantages of the invention will become apparent as the invention becomes better understood by reference to the following detailed description when considered in conjunction with the accompany drawings.

DETAILED DESCRIPTION OF THE INVENTION

Figure 1:
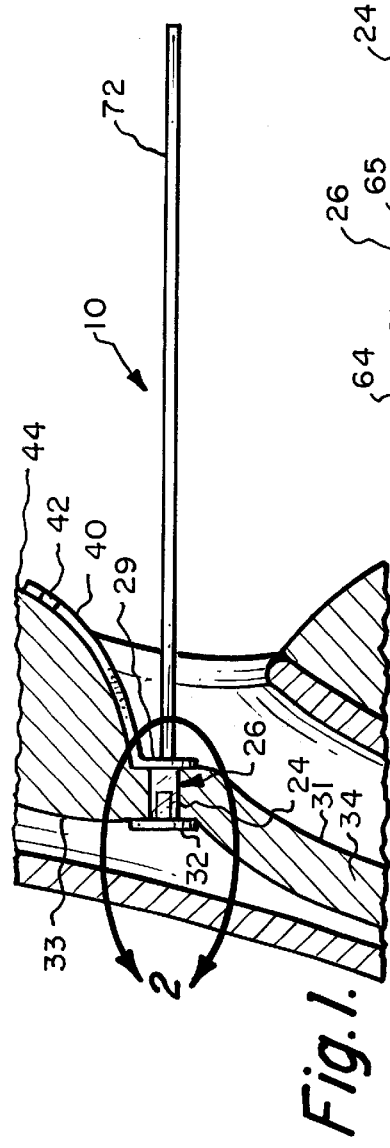
FIG. 1 is a schematic view in section of a brush according to the invention inserted into a voice prosthesis resident in a stoma.
Figure 2:
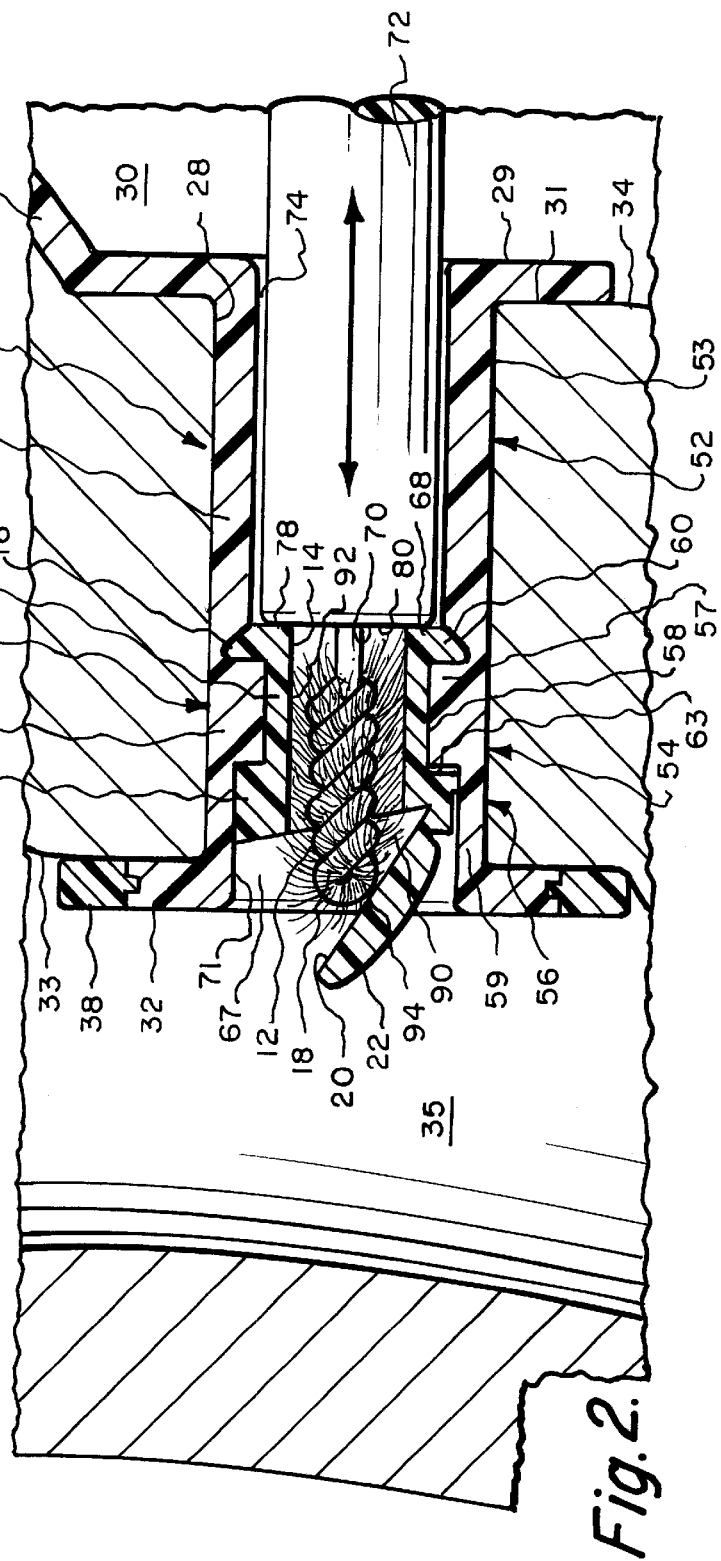
FIG. 2 is an enlarged view in section taken along line 2 of FIG. 1.

Referring now to FIGS. 1 and 2 a brush 10 is shown with the bristle portion 12 disposed within a central passage 14 through a cartridge 16 with the end 18 of the brush resting against the inner face 20 of the valve 22. A soft body 24 of the voice prosthesis 26 surrounds the cartridge 16. The prostheses 26 is inserted in a fistula 28 through the esophageal wall 34 with a proximal flange 29 engaging the outer wall 31 of the trachea 30 and the distal flange 32 in engagement with the surface 33 on the esophagus side of the fistula 28. The distal flange 32 can include radiopague indications 38 for confirming that flange 32 is correctly deployed following prosthesis 32 insertion. The proximal flange 29 can have a flexible tab 40 with aperture 42 which can be attached to an insertion tool, not shown. The tab 40 can be removed or taped to the neck 44 of the user.

The front tracheal flange 29 and rear retention esophageal flange 32 are connected to the ends of the soft body 24. The body 24, front flange 29 and rear flange 32 are preferably a single molded, unitary structure formed from a biocompatible medical grade elastomer such as a silicone or polyurethane resin, suitably approximately 50 durometer. Since the material is transparent and the prosthesis structure is small, the prosthesis is difficult to visualize and handle. Therefore, the molding material sometimes contains a small amount, from 0.1 to 0.5% of a biocompatible pigment to aid in seeing the device. The pigment can be a heavy metal salt such as barium sulfate. The cartridge 16 is formed of an inert, self-lubricating polymer, suitably a fluorinated resin such as TEFLON (polytetrafluoroethylene) or a polyalkylene resin such as polyethylene or polypropylene, suitably DELRIN or KYNAR.

The tubular body 24 has a first section 52 having a wall 53 of a first thickness, a central section 54 having a wall 57 of a greater thickness and a third wall section 56 having a wall 59 of reduced thickness. The central wall section 54 forms a cylindrical boss 61 which is received in an annular channel 58 formed in the outer wall of the cartridge 16.

The hollow cartridge 2 has a front flange 60 and a rear flange 64 connected to cylindrical section 65 forming the central passage 14 between the flanges 60, 64. The cartridge 16 is assembled with the body 24 by inserting the front flange 60 of the cartridge 16 into the rear opening 67 of the channel 71 through the body 24 and forcing it through the central channel 71 of the body 24 compressing the boss 61 until the front flange 60, enters the central channel 71. The front flange 60 seats against the end wall 68 of the boss 61 and the rear flange 64 seats against the rear wall 59 of the boss 61.

The end face 70 of the rod 72 has a diameter only slightly less than the diameter of the central bore 74 through proximal portion 76 of the soft body 24 and larger than the central passage 14 through the cartridge 16 such that the distal end face 78 of the cartridge 16 engages the peripheral portion 80 of the end face 70 of the rod 72 and prevents it from any further movement.

The length of the bristle portion 12 from the end face 70 of the rod to the end 18 of the brush is less than the distance from the end face 70 to the opposed surface 33 of the esophagus 35. The length of the bristle portion 12 need only be sufficient for the bristles 90 to engage the inner face 20 of the valve 22. The length of the bristles 90 are sufficient to contact and clean the inner wall 92 of the cartridge 16 and the inner wall of the front portion 76 of the soft body. The bristles 90 are shown mounted in a twisted wire 94. The wire 94 can be potted into the plastic rod 72 which forms the handle of the brush 10. The bristles 90 could also be potted directly into a smaller diameter end section of the rod 72.

It is to be realized that only preferred embodiments of the invention have been described and that numerous substitutions, modifications and alterations are permissible without departing from the spirit and scope of the invention as defined in the following claims.

What is claimed is:

1. A brush for a voice prosthesis having a soft, hollow outer body with a first channel through said body, said first channel having a diameter and a proximal end, and a hollow, hard cartridge having a proximal end and having a second channel with a smaller diameter than the diameter of said first channel forming a second wall surface, said cartridge being seated in said first channel rearward of the proximal end of the first channel forming a wall first wall surface extending into the channel, the brush comprising:

a rod portion having a distal face with a diameter less than the diameter of the first channel and greater than the diameter of the second channel through the cartridge, whereby said distal face abuts and is stopped by the proximal end of the cartridge, a brush portion extending distally from the distal face of the rod, said portion having bristles having a length at least capable of contacting and cleaning the wall surface of said first channel and of entering the cartridge channel and contacting and cleaning the wall surface of the second channel.

2. A brush according to claim 1 in which the brush portion extends no further than about the distance from the proximal face of the cartridge to the distal end of the soft body of the voice prosthesis.

3. A brush according to claim 2 in which the voice prosthesis has a distal end, the distal end of the prosthesis contains a hinged valve and the brush portion extends distally no further than about the distal end of the voice prosthesis.

4. A brush according to claim 1 in which the brush portion contains bristles mounted on a reduced diameter brush portion of the brush.

5. A brush according to claim 4 in which the bristles are mounted in a twisted wire.

* * * * *